US006251400B1

(12) United States Patent
Guthrie et al.

(10) Patent No.: US 6,251,400 B1
(45) Date of Patent: *Jun. 26, 2001

(54) COMPOSITIONS AND METHODS OF TREATMENT OF NEOPLASTIC DISEASES AND HYPERCHOLESTEROLEMIA WITH CITRUS LIMONOIDS AND FLAVONOIDS AND TOCOTRIENOLS

(75) Inventors: Najla Guthrie; Elzbieta Maria Kurowska; Kenneth Kitchener Carroll, all of London (CA)

(73) Assignee: KGK Synergize INC, London (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/938,640

(22) Filed: Sep. 26, 1997

(51) Int. Cl.[7] .......................... A61K 35/78; A61K 47/00; A61K 31/355; A23L 2/00
(52) U.S. Cl. .................. 424/195.1; 424/439; 426/599; 426/615; 426/648; 514/458; 514/824
(58) Field of Search ................ 424/195.1, 439; 426/599, 648, 615; 514/824, 458

(56) References Cited

U.S. PATENT DOCUMENTS

| 3,993,793 | * | 11/1976 | Finney ................... 426/565 |
| 4,368,213 | * | 1/1983 | Hollenbach et al. ........ 426/590 |
| 5,616,355 | * | 4/1997 | Haast et al. ............. 426/384 |

FOREIGN PATENT DOCUMENTS

| 5054883 | * | 4/1980 | (JP) . |
| 7135922 | * | 5/1995 | (JP) . |
| 8283154 | * | 10/1996 | (JP) . |

OTHER PUBLICATIONS

Carroll et al. FASEB J. vol. 9 (4), p. A868, Meeting abstract, 1995.*
Formica et al. Food Chem. Toxicol. vol. 33 (12), pp. 1061–1080, abstract enclosed, 1995.*
Choi et al. J. Nat. Prod.—Lloydia. vol. 54 (1), pp. 218–224, abstract enclosed, 1991.*
Lam, et al., 1994, Food Technology, 48:104–108.
Hasegawa, S. et al., 1994, in Food Phyochemicals for Cancer Prevention I, eds M–t. Huang et al., American Chemical Society, 198–207.
Shin Hasegawa and Masaki Miyake, "Biochemistry and Biological Functions of Citrus Limonoids", Food Rev. Int., 12 (4), 413–435 (1996).
Hertog, M.G. et al., 1993, Lancet: 342, 1007–1011.
Kurowska, E.M. et al., 1990, J. Nutr. 120:831–836.
Guthrie N. et al., 1996, Proc. Am. Inst. Cancer Res., Abs. #8.
Cummings, F.J. et al, 1985, Ann. Intern. Med. 103;324.
Boring, C.C. et al., 1993, CA Cancer J. Clin. 43:7.
Sattin, R.W. et al., 1985, JAMA 253 : 1908.
Schatzkin A. et al., 1987, N. Engl. J. Med. 316 : 1169.
Carroll, K.K., 1980, J. Env.Pathol. Tox. 3: 253–271.
Castelli, W.P. et al., 1986, JAMA 256 : 2835.
Report of the National Education Program Expert Panel on Detection, Evaluation, and Treatment of High Blood Cholesterol in Adults, 1988, Arch. Intern. Med. 148 : 36.

* cited by examiner

Primary Examiner—Leon B. Lankford, Jr.
Assistant Examiner—Christopher R. Tate

(57) ABSTRACT

Compositions and methods for the prevention and treatment of neoplastic diseases and hypercholesterolemia are described. Individuals at a high risk of developing or having neoplasia or hypercholesterolemia undergoing conventional therapies may be treated with an effective dose of triterpene derivatives in citrus limonoids, polyphenolic flavonoid citrus compounds, tocotrienols or a combination of these agents.

10 Claims, 4 Drawing Sheets

Figure 1:
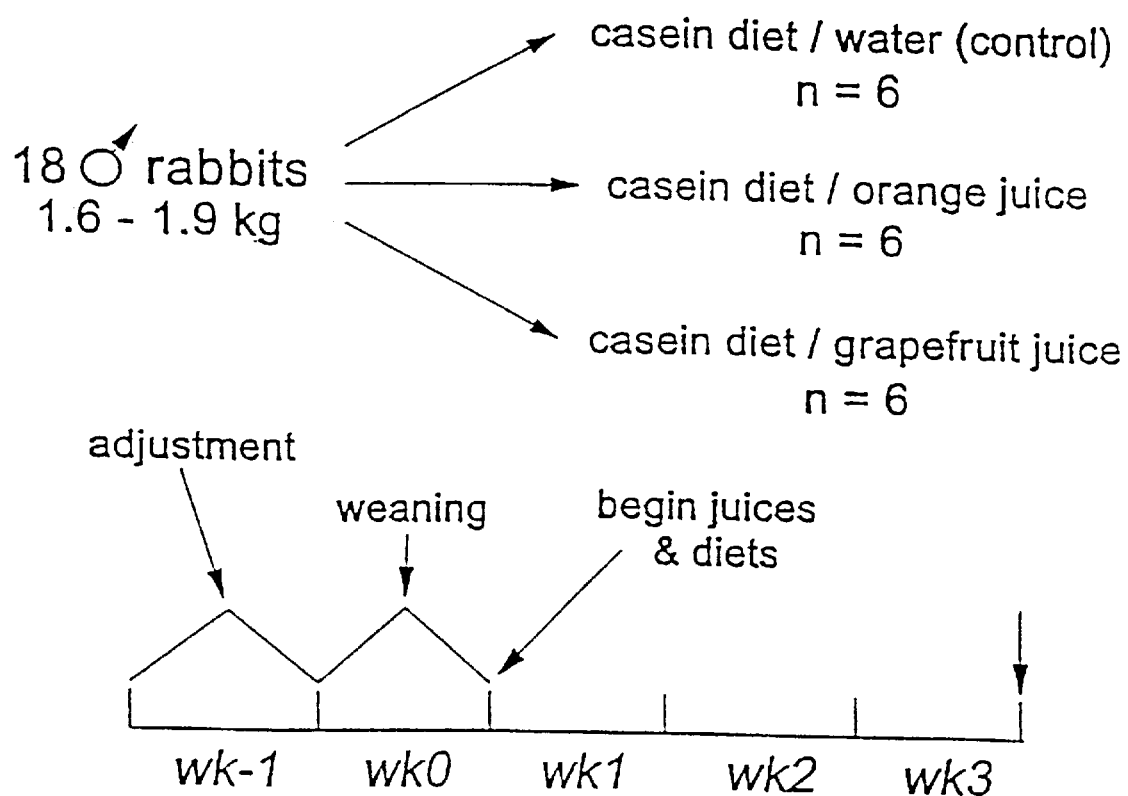

COMPOSITIONS AND METHODS OF TREATMENT OF NEOPLASTIC DISEASES AND HYPERCHOLESTEROLEMIA WITH CITRUS LIMONOIDS AND FLAVONOIDS AND TOCOTRIENOLS

1. INTRODUCTION

The present invention relates to compositions and methods for the prevention and treatment of oncogenic disorders, atherosclerosis and hypercholesterolemia, with citrus limonoids, flavonoids and/or tocotrienols. Limonoids are a group of chemically related triterpene derivatives found in the Rutaceae and Meliaceae families. Citrus limonoids are among the bitter principles in citrus juices such as lemon, lime, orange and grapefruit. Flavonoids are polyphenolic compounds that occur unbiquitously in plant foods especially in orange, grapefruit and tangerine. Tocotrienols are present in palm oil and are a form of vitamin E having an unsaturated side chain. In the practice of the cancer prevention and/or treatment of the invention the limonoids, flavonoids and tocotrienols are used to inhibit the development and proliferation of cancer cells. Preferred compositions of the invention are those which specifically or preferentially prevent transformation of preneoplastic cells to tumor cells, and prevent or inhibit tumor cell proliferation, invasion and metastasis without general cytotoxic effects. In the practice of the prevention and/or treatment of atherosclerosis and/or hypercholesterolemia, the flavonoids, limonoids and tocotrienols are used to inhibit production of cholesterol, low-density lipoprotein (LDL) and apo B protein. Compositions comprising citrus flavonoids, limonoids and tocotrienols are used to prevent and/or inhibit production of cholesterol, LDL and apoB.

2. BACKGROUND

2.1. Citrus Limonoids

Limonoids are a group of chemically related triterpene derivatives found in the Rutaceae and Meliaceae families. Limonoids are among the bitter principles found in citrus fruits such as lemons, lime, orange and grapefruit. They are also present as glucose derivatives in mature fruit tissues and seed, and are one of the major secondary metabolites present in Citrus. Limonoids have been found to have anti-carcinogenic activity in laboratory animals. The furan moiety attached to the D-ring is specifically responsible for detoxifying of the chemical carcinogen by induction of the liver glutathione-S-transferase enzyme system (Lam, et al., 1994, Food Technol. 48:104–108).

Citrus fruit tissues and by-products of juice processing such as peels and molasses are sources of limonoid glucosides and citrus seeds contain high concentrations of both limonoid aglycones and glucosides. Limonoid agylycones in the fruit tissues gradually disappear during the late stages of fruit growth and maturation.

Thirty-eight limonoid aglycones have been isolated from Citrus. The limonoids are present in three different forms: the dilactone (I) is present as the open D-ring form (monolactone), the limonoate A-ring lactone (II) and the glucoside form (III). Only the monolactones and glucosides are present in fruit tissues. (Hasegawa S. et al., 1994, in Food Phytochemicals for Cancer Prevention I, eds M-T. Huang et al., American Chemical Society, 198–207).

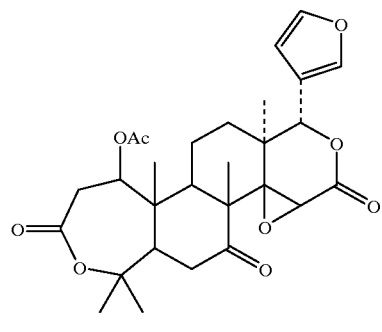

Nomilin

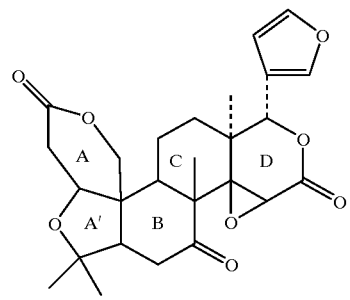

Limonin

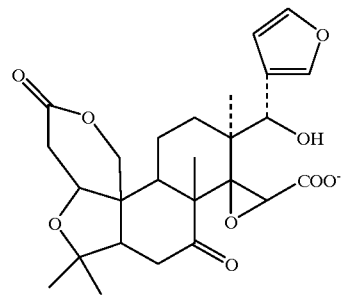

Limonoate A-ring lactone

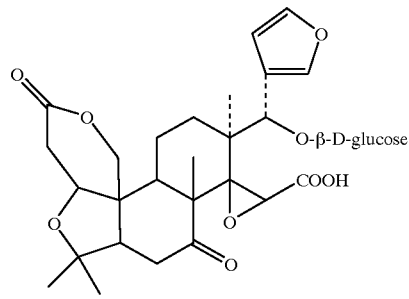

Limonin 17-β-D-glucopyranoside

Compound III is the predominant limonoid glucoside found in all juice samples. In orange juice it comprises 56% of the total limonoid glucosides present, while in grapefruit and lemon juices, it comprises an average of 63% to 66% respectively. Procedures for the extraction and isolation of both aglycones and glucosides have been established to obtain concentrated sources of various limonoids (Lam, L. K. T. et al., 1994, in Food Phytochemicals for Cancer Prevention, eds. M. Huang, T. Osawa, C. Ho and R. T. Rosen, ACS Symposium Series 546, p 209). The use of limonoids alone or in combination with a citrus flavonoid, tocotrienol, a cancer chemotherapeutic agent, or a combination of any one of these agents, has not been reported for the prevention and treatment of neoplastic diseases.

2.2. Citrus Flavonoids

Epidemiological studies have shown that flavonoids present in the Mediterranean diet may reduce the risk of death from coronary heart disease (Hertog, M. G. et al., 1993, Lancet: 342, 1007–1011). Soybean isoflavones for example, genistein, which is a minor component of soy protein preparations may have cholesterol-lowering effects (Kurowska, E. M. et al., 1990, J. Nutr. 120:831–836). The flavonoids present in citrus juices such as orange and grapefruit include, but are not limited to, hesperetin and naringenin respectively. The use of flavonoids from citrus juices alone or in combination with a citrus limonoid, tocotrienol, a cholesterol—lowering drug, or a combination of any one of these agents, has not been reported for the treatment of hypercholesterolemia.

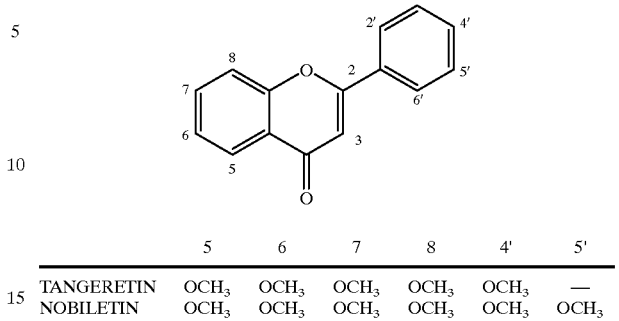

| | 5 | 6 | 7 | 8 | 4' | 5' |
|---|---|---|---|---|---|---|
| TANGERETIN | OCH$_3$ | OCH$_3$ | OCH$_3$ | OCH$_3$ | OCH$_3$ | — |
| NOBILETIN | OCH$_3$ | OCH$_3$ | OCH$_3$ | OCH$_3$ | OCH$_3$ | OCH$_3$ |

2.3 Tocotrienols in Palm Oil

Tocotrienols are present in palm oil and are a form of vitamin E having an unsaturated side chain. They include, but are not limited to alpha-tocotrienol, gamma-tocotrienol or delta-tocotrienol.

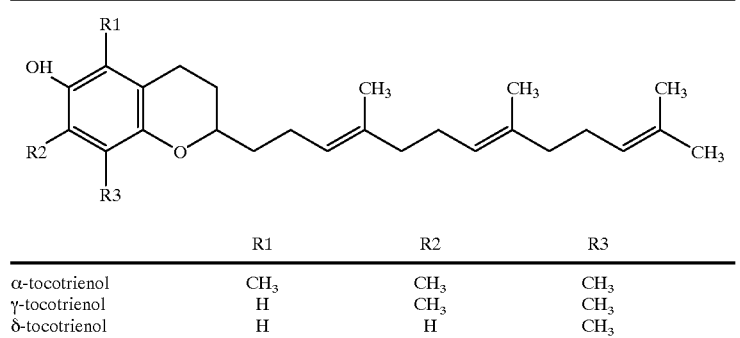

| | R1 | R2 | R3 |
|---|---|---|---|
| α-tocotrienol | CH$_3$ | CH$_3$ | CH$_3$ |
| γ-tocotrienol | H | CH$_3$ | CH$_3$ |
| δ-tocotrienol | H | H | CH$_3$ |

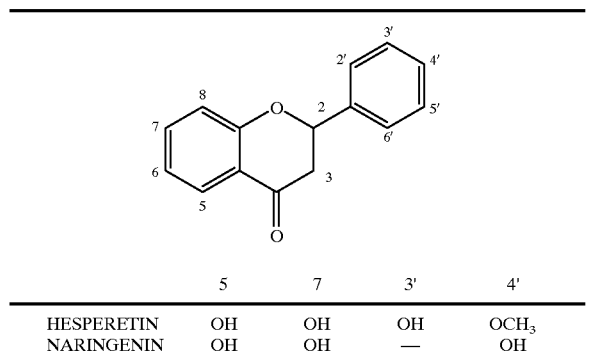

| | 5 | 7 | 3' | 4' |
|---|---|---|---|---|
| HESPERETIN | OH | OH | OH | OCH$_3$ |
| NARINGENIN | OH | OH | — | OH |

The flavonoids preset in tangerine include, but are not limited to tangeretin or nobiletin. These flavonoids were found to inhibit growth of both estrogen receptor-negative (ER−) and positive (ER+) breast cancer cells in culture and act synergistically with tamoxifen and tocotrienols (Guthrie N. et al., 1996, Proc. Am. Inst. Cancer Res., Abs. #8).

2.4. Cancer Growth and Chemotherapy

Cancer is a disease of inappropriate tissue accumulation. Chemotherapeutic agents share one characteristic: they are usually more effective in killing or damaging malignant cells than normal cells. However, the fact that they do harm normal cells indicates their potential for toxicity. Animal tumor investigations and human clinical trials have shown that drug combinations produce higher rates of objective response and longer survival than single agents. Combination drug therapy is, therefore, the basis for most chemotherapy employed at present (DeVita, V. T. et.al., 1995, Cancer 35:98).

Cancer treatment requires inhibitions of a variety of factors including tumor cell proliferation, metastatic dissemination of cancer cells to other parts of the body, invasion, tumor-induced neovascularization, and enhancement of host immunological responses and cytotoxicity. Conventional cancer chemotherapeutic agents have often been selected on the basis of their cytotoxicity to tumor cells. However, some anticancer agents have adverse effects on the patient's immune system. Thus it would be greatly advantageous if a cancer therapy or treatment could be developed that would afford non-cytotoxic protection against factors that might lead to progression of tumors.

Because hormone therapy as well as chemotherapy is effective in controlling advanced breast cancer, it has been used as an adjuvant to mastectomy in primary breast cancer. Patients with ER+ or ER− tumors benefit from adjuvant chemotherapy. However, tamoxifen used alone as an adjuvant to mastectomy for breast cancer shows benefit in extending disease-free and overall survival (Cummings, F. J. et al., 1985, Ann. Intern. Med. 103;324).

3. SUMMARY OF THE INVENTION

The present invention is directed to a method for the prevention and/or treatment of neoplastic diseases, which involves using a composition of citrus limonoids to treat an individual at high risk for, or suffering from cancer.

The present invention is also directed to a method for the prevention and/or treatment of breast cancer, which involves using a composition of citrus limonoids and citrus flavonoids to an individual at high risk or suffering from cancer.

The present invention is also directed to a method for the prevention and/or treatment of breast cancer, which involves using a composition of citrus limonoids, citrus flavonoids and tocotrienols to an individual at high risk or suffering from cancer.

The present invention is also directed to a method for the prevention and/or treatment of breast cancer, which involves using a composition of citrus limonoids, citrus flavonoids, tocotrienols or tamoxifen to an individual at high risk or suffering from breast cancer.

The present invention is directed to a method for the prevention and for treatment of neoplastic diseases, which involves using an effective dose of a combination of citrus limonoids, flavonoids, and/or tocotrienols with or without conventional chemotherapy or hormonal and/or radiation therapy or surgery, to treat a patient suffering from cancer.

The present invention is also directed to a method for preventing immune suppression and toxicity induced by anticancer chemotherapeutic agents, using an effective dose of citrus limonoids alone or in combination with flavonoids, to treat a patient suffering from cancer.

The present invention further provides methods to treat cardiovascular disease, atherosclerosis or hypercholesterolemia, that is, lower serum cholesterol, apo-B and LDL cholesterol, using a composition of citrus flavonoids to treat an individual at high risk of or suffering from cardiovascular disease, for example, atherosclerosis or hypercholesterolemia.

The present invention further provides methods to treat hypercholesterolemia, that is, lower serum cholesterol, apo-B and LDL cholesterol, using a composition of citrus flavonoids, citrus limonoids, tocotrienols, a cholesterol-lowering drug or a combination of these agents to treat an individual at high risk of or suffering from hypercholesterolemia.

4. DETAILED DESCRIPTION OF FIGURES

FIG. 1 depicts the design of the animal experiment.

Figure 2:
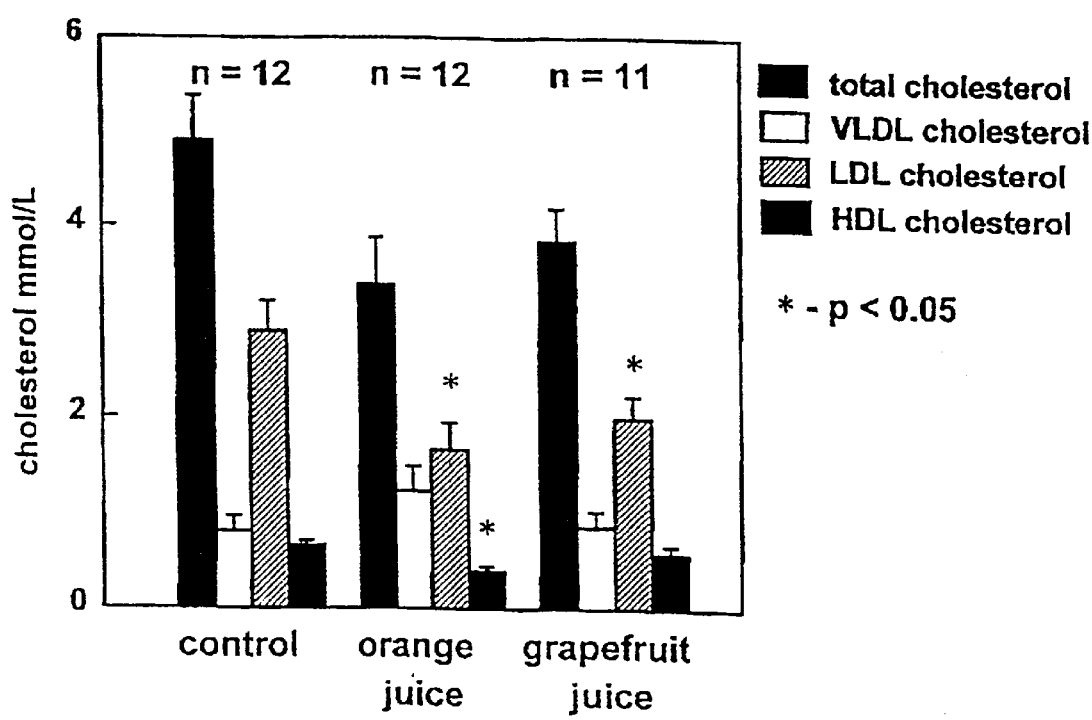

FIG. 2 describes the effect of citrus juices on total and liprotein cholesterol concentrations in rabbits fed casein diet.

Figure 3A:
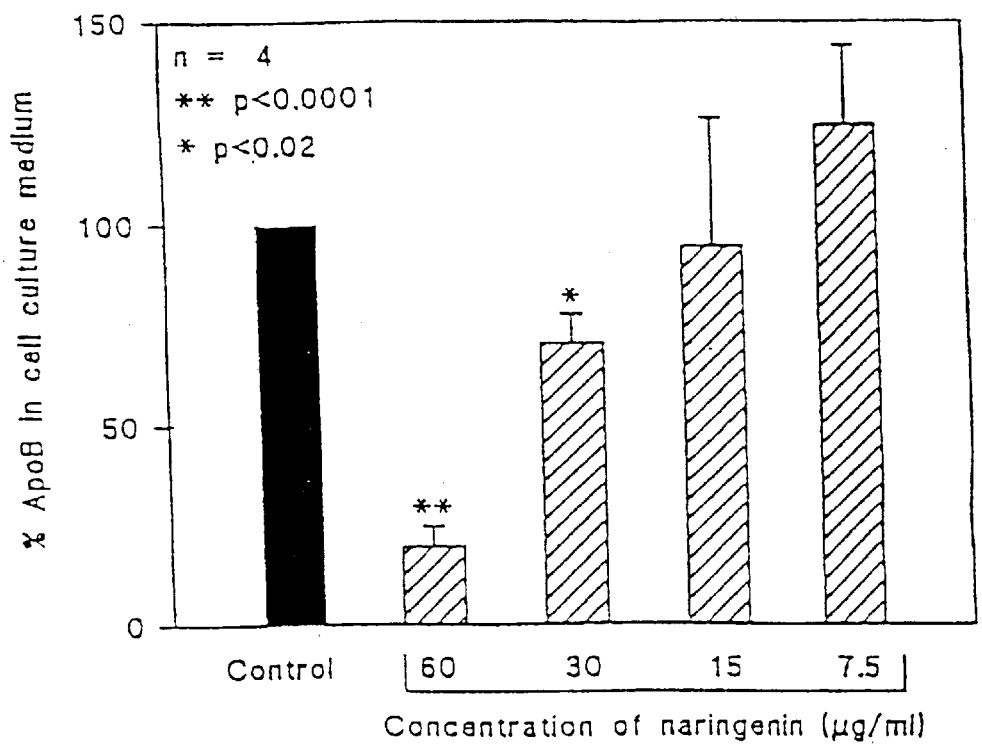
Figure 3B:
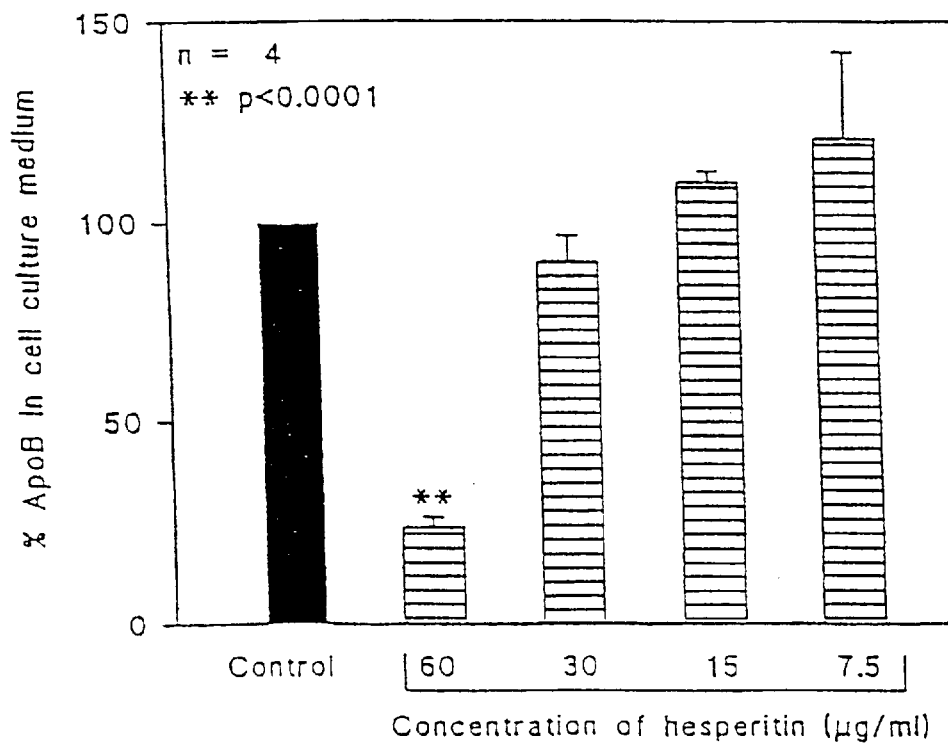

FIG. 3 describes the overall apoB production in HepG2 cells exposed to increasing concentrations of naringenin (FIG. 3a) and hesperetin (FIG. 3b).

Figure 4:
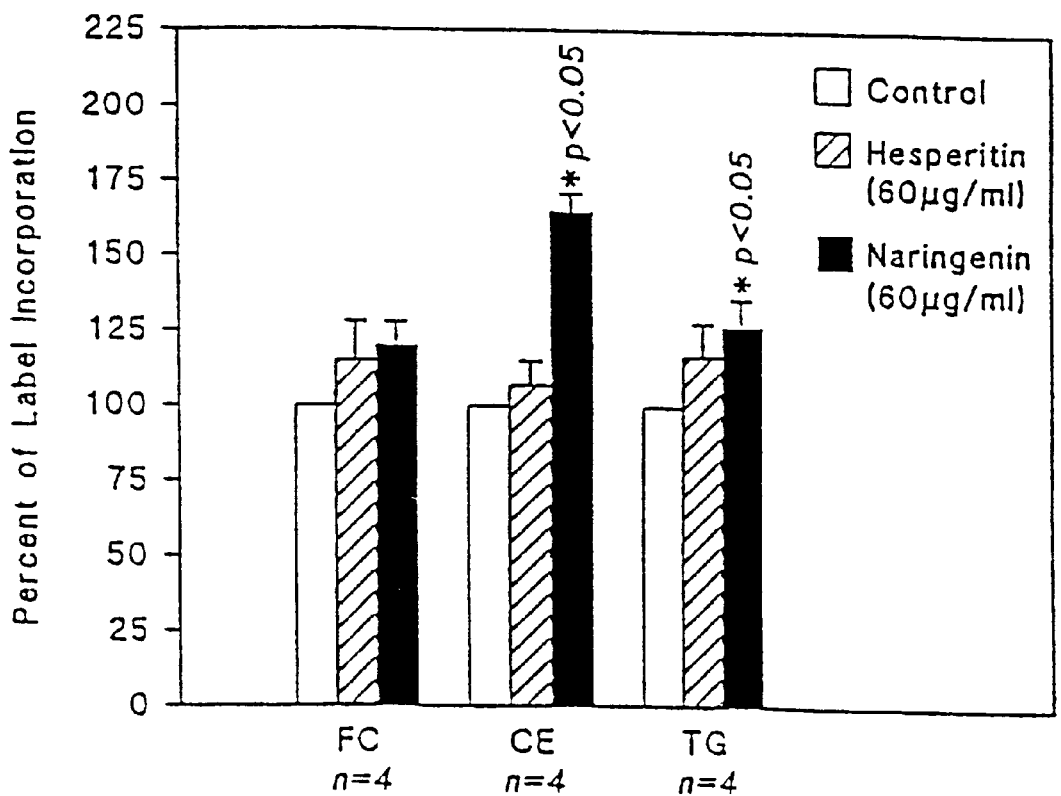

FIG. 4 describes changes in incorporation of 14C-acetate into cellular lipids in HepG2 cells incubated with hesperetin and naringenin.

5. DETAILED DESCRIPTION OF THE INVENTION

The method of the invention involves administering an effective dose of a citrus limonoid alone or in combination with citrus flavonoids and tocotrienols, tamoxifen, a chemotherapeutic agent, or a specific combination of these agents, to an individual who is identified as being at enhanced risk for cancer and/or as having cancer, in order to prevent and/o treat cancer.

It may be that the ability of citrus limonoids alone or in combination with flavonoids or tocotrienols, to inhibit tumor cell proliferation, to inhibit the metastatic spread of tumor cells or to prevent immuno-suppression and toxicity induced by chemotherapeutic agents, contributes to their effectiveness in the prevention and treatment of neoplastic diseases. These possible mechanisms of action are in no way meant to limit the scope of the invention and are presented purely for explanatory and/or illustrative purposes.

The method of the invention also involves administering an effective dose of a citrus flavonoid alone or in combination with a citrus limonoid, tocotrienol or a cholesterol lowering drug, to an individual who is identified as being at enhanced risk for atherosclerosis, cardiovascular disease or hypercholesterolemia and/or as having atherosclerosis, cardiovascular disease or hypercholesterolemia, in order to prevent and treat hypercholesterolemia.

It may be that the ability of citrus flavonoids to lower cholesterol, to inhibit liver cholesterol sythesis, inhibit LDL cholesterol and apo-B synthesis, contributes to their effectiveness in the reduction of atherosclerosis and hypercholesterolemia and lowering the risk of cardiovascular disease. These possible mechanisms of action are in no way meant to limit the scope of the invention and are presented purely for explanatory and/or illustrative purposes.

5.1 Cancer

Cancer is the second leading cause of death in the United States, after heart disease (Boring, C. C. et al., 1993, CA Cancer J. Clin. 43:7), and develops in one in three Americans, and one of every four Americans dies of cancer. Cancer can be viewed as a breakdown in the communication between tumor cells and their environment, including their normal neighboring cells. Signals, both growth-stimulatory and growth-inhibitory, are routinely exchanged between cells within a tissue. Normally, cells do not divide in the absence of stimulatory signals, and likewise, will cease dividing in the presence of inhibitory signals. In a cancerous, or neoplastic state, a cell acquires the ability to "override" these signals and to proliferate under conditions in which normal cells would not grow.

In addition to unhindered cell proliferation, cells must acquire several traits for tumor growth to occur. For example, early on in tumor development, cells must evade the host immune system. Further, as tumor mass increases, the tumor must acquire vasculature to supply nourishment and remove metabolic waste. Additionally, cells must acquire an ability to invade adjacent tissue, and ultimately cells often acquire the capacity to metastasize to distant sites.

Cancer of the breast is the most common form of malignant disease occurring among women of the Western World, and it is the most common cause of death among those who are between 40 and 45 years of age.

In North American women, characteristics that are associated with a threefold to fourfold increase in risk for breast cancer include (1) first-degree female family members (mothers and sisters) who had breast cancer, (2) prior breast cancer, (3) nulliparity, (4) age greater than 30 years at first pregnancy and (5) early menarche or late menopause (Sattin, R. W. et al., 1985, JAMA 253:1908). International studies have demonstrated a positive correlation between per capita consumption of fat and alcohol (Schatzkin A. et al., 1987, N. Engl. J. Med. 316:1169) and the incidence of breast cancer. (Carroll,K. K., 1980, J. Env.Pathol. Tox. 3:253–271). Several studies have linked the consumption of fresh fruits and vegetables, and vitamin E with reduced risk of developing cancer, including breast cancer (Steinmetz, K. A. et al., 1991, Cancer Causes Control 2:427–442). Although this protective effect has been generally attributed to the antioxidant capacities of vitamin C and beta-carotene present in these foods, it may be related to other phytochemical constituents such as citrus limonoids and flavonoids. The use of limonoids, flavonoids or tocotrienols alone or in combination with each other or with a cancer chemo-therapeutic agent has not been reported for the prevention and treatment of neoplastic diseases.

The present invention provides a number of different citrus limonoids comprising, but not limited to, limonin, nomilin, limonin glucoside or glucoside mixture, flavonoids comprising nobiletin or tangeretin and tocotrienol comprising alpha-tocotrienol, gamma-tocotrienol or delta-tocotrienol.

Cancers that can be prevented and/or treated by the compositions and methods of the present invention include, but are not limited to, human sarcomas and carcinomas, e.g. carcinomas, e.g., colon carcinoma, pancreatic cancer, breast cancer, ovarian cancer, prostate cancer, fibrosarcoma, myxosarcoma, liposarcoma, chondrosarcoma, osteogenic sarcoma, chondroma, angiosareoma, endotheliosarcoma, lymphangiosareoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. Specific examples of such cancers are described in the sections below.

5.2 Atherosclerosis and Hypercholesterolemia

In the United States, the complications of arteriosclerosis account for about one half of all deaths and for about one third of deaths in persons between 35 and 65 years of age. Atherosclerosis, or the development of atheromatous plaques in large and medium-sized arteries, is the most common form of arteriosclerosis. Many factors are associated with the acceleration of atherosclerosis, regardless of the underlying primary pathogenic change, for example, age, elevated plasma cholesterol level, high arterial blood pressure, cigarette smoking, reduced high-density lipoprotein (HDL) cholesterol level, or family history of premature coronary artery disease.

The risk of death from coronary artery disease has a continuous and graded relation to total serum cholesterol levels greater than 180 mg/dl (Stamler, J. et al., 1986, JAMA 256:2823). Approximately one third of adults in the United States have levels that exceed 240 mg/dl and, therefore, have a risk of coronary artery disease that is twice that of people with cholesterol levels lower than 180 mg/dl. Acceleration of atherosclerosis is principally correlated with elevation of LDL, or beta fraction, which is rich in cholesterol but poor in triglycerides. Elevation of HDL or alpha fraction, has a negative correlation with atherosclerosis (Castelli, W. P. et al., 1986, JAMA 256:2835). HDL exerts a protective effect and the ratio of total cholesterol to HDL cholesterol is a better predictor of coronary artery disease than the level of either alone. Total cholesterol levels are classified as being desirable (<200 mg/dl), borderline high (200–239 mg/dl), or high (>240 mg/dl) (Report of the National Education Program Expert Panel on Detection, Evaluation, and Treatment of High Blood Cholesterol in Adults, 1988, Arch. Intern. Med. 148:36)

Advances in the study of cholesterol metabolism and coronary disease have initiated an era of increased emphasis on preventive therapy. New guidelines for the detection and treatment of high blood cholesterol in adults recommend that patients with high cholesterol levels or with borderline-high levels and two or more additional risk factors should have a measurement of LDL. LDL cholesterol levels are then classified as borderline-high risk (130–159 mg/dl) or high risk ($\geq$160 mg/dl). Dietary treatment is recommended for those patients with high-risk levels of LDL and for those with borderline-high risk levels who have two or more additional risk factors. Drug treatment is recommended for all patients with LDL levels greater than 189 mg/dl and for those patients with LDL cholesterol levels between 159 and 189 mg/dl who have two or more additional risk factors. Among the many drugs that have been used to reduce serum cholesterol levels are cholestyramine, colestipol, clofibrate, gemfibrozil and lovastatin. The use of flavonoids alone or in combination with citrus limonoids, tocotrienols or a cholesterol-lowering drug has not been reported for the treatment of hypercholestrolemia.

5.3 Dosage and Formulations

Citrus limonoids, citrus flavonoids or tocotrienols may be formulated into pharmaceutical preparations for administration to mammals for prevention and treatment of neoplastic diseases and/or cardiovascular disease, hypercholesterolemia or atherosclerosis.

Many of the citrus limonoids, flavonoids or tocotrienols may be provided as compounds with pharmaceutically compatible counterions, a form in which they may be soluble.

The therapeutic compounds or pharmaceutical compositions may be administered intravenously, intraperitoneally, subcutaneously, intramuscularly, intrathecally, orally, rectally, topically or by aerosol.

Formulations suitable for oral administration include liquid solutions of the active compound dissolved in diluents such as saline, water or PEG 400; capsules or tablets, each containing a predetermined amount of the active agent as solid, granules or gelatin; suspensions in an approximate medium; and emulsions.

Formulations suitable for parenteral administration include aqueous and non-aqueous isotonic sterile solutions, which contain buffers, antioxidants and preservatives. The formulations may be in unit dose or multi-dose sealed containers.

Patient dosages for oral administration of citrus limonoids range from 1–500 mg/day, commonly 1–100 mg/day, and typically from 1–100 mg/day. Stated in terms of patient body weight, usual dosages range from 0.01–10 mg/kg/day, commonly from 0.01–2.0 mg/kg/day, typically from 0.01 to 2.0 mg/kg/day.

Patient dosages for oral administration of citrus flavonoids range from 200–5000 mg/day, commonly 1000–2000 mg/day, and typically from 500–1500 mg/day. Stated in terms of patient body weight, usual dosages range from 15–70 mg/kg/day, commonly from 15–30 mg/kg/day, typically from 7–21 mg/kg/day.

Patient dosages for oral administration of tocotrienols range from 1–1200 mg/day, commonly 1–100 mg/day, and typically from 1–60 mg/day. Stated in terms of patient body weight, usual dosages range from 0.01–20 mg/kg/day, commonly from 0.01–2.0 mg/kg/day, typically from 0.01 to 1.0 mg/kg/day.

Dosage amount and interval may be adjusted individually to provide plasma levels of the active moiety which are sufficient to maintain the anti-proliferative and anti-metastatic effects.

Alternatively, one may administer the compound in a local, rather than oral manner, for example, via injection of the compound directly into a tumor, often in a depot or sustained release formulation.

A variety of delivery systems for the pharmacological compounds may be employed, including, but not limited to, liposomes and emulsions. The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Furthermore, one may administer the agent in a targeted drug delivery system, for example, in a liposome coated with tumor-specific antibody. The liposomes will be targeted to and taken up selectively by the tumor.

In cases of local administration or selective uptake, the effective local concentration of the drug may not be related to plasma concentration.

6. EXAMPLE

Effects of Citrus Limonoids, Flavonoids, Tocotrienols and/or Tamoxifen in MDA-MB-435 and MCF-7 Breast Cancer Cells (a) The effect of citrus limonoids, nomilin, limonin and limonin glucoside on the proliferation and growth of MDA-MB-435 estrogen receptor-negative human breast cells was studied in vitro, as measured by the incorporation of [$^3$H] Thymidine.

Materials: Limonin, nomilin, limonin glucosides and a mixture of glucosides (limonin glucoside-30% nomilin glucoside-12.7%, nomilinic acid glucoside-35.%, obacunone glucoside-8.2%, deacetylnomilin glucoside-6.6% and deacetylnomilinic acid glucoside-8.7%) were obtained from Dr. Shin Hasagawa at the United States Department of Agriculture, Agricultural Research Service, Albany, Calif. Tissue culture medium and fetal calf serum were purchased from Gibco, Burlington, ON. [$^3$H] Thymidine was purchased from ICN, Irvine, Calif.

Cell Culture: MDA-MB-435 cells (human breast cancer cells) were maintained at 37° C. in a minimum essential medium, supplemented with 10% (v/v) fetal bovine serum. The medium was equilibrated with a humidified atmosphere of 5% $CO_2$. Stock cultures were seeded at a density of $2\times10^4$ cells/ml and allowed to multiply for 48 to 72 hours.

Incorporation of [3H] Thymidine Into DNA: MDA-MB-435 cells were plated at $2\times10^4$ cells/well in 96-well, flat bottomed, culture plates in a total volume of 200 μL of medium and incubated at 37° C. for 48 hours with or without test compounds. [$^3$H] Thymidine (0.5 μCi/well) was then added and after 4 hours the cells were harvested onto a glass fibre filter paper using a semiautomatic 12-well cell harvester (Skatron Inc., Sterling, Va.). Radioactivity on the filter paper was counted using Scinteverse in a liquid scintillation counter.

Growth Experiment: MDA-MB-435 cells were plated at $1\times10^4$ cells/dish in 60 mm dishes with or without test compounds. The cells were removed by trypsinization at specified times and counted using a hemocytometer.

Viability of Cells: Viability of cells was measured by MTT assay (Hansen, M. B. et al., J. Immunol. Meth., 119, 203–210, 1989). In this assay a tetrazolium salt,3-[4,5-dimethylthiazole]-2,5-diphenyltetrazolium bromide, MTT, is reduced to a blue formazan product by mitochondrial dehydrogenases that are active in living cells. The intensity of the blue colour developed is a measure of cell viability. MDA-MB-435 cells ($8\times10^4$/well) were seeded in 96-well, flat-bottomed tissue culture plates with various concentrations of the test compounds, in a total volume of 200 μl/well of medium. Forty-eighty hours later, MTT (25 μL of 5 mg/ml) was added to each well. After 3 hours, 100 μl of extraction buffer, consisting of 20% SDS dissolved in a 50% DMF, 50% water solution at pH 4.0, was added. The blue colour formed was measured at 570 nm in a Dynatech MRX Microplate Reader. The percentage of cells surviving was determined by comparing the absorbance of the treated cells with that of the control.

Results: Nomilin was the most effective, at inhibiting the proliferation of the breast cancer cells, having an IC50 of 0.4 μg/ml. Limonin and limonin glucoside inhibited these cells with IC50s of 12.5 and 75 μg/ml respectively. A mixture of citrus limonoids was tested and gave an even lower IC50 of 0.08 μg/mL. Table 1.

TABLE 1

Inhibition of Proliferation of MDA-MB-435 Estrogen Receptor-Negative Human Breast Cancer Cells by Citrus Limonoids

| LIMONOIDS | $IC_{50}$ (μg/ml) |
| --- | --- |
| Nomilin | 0.4 |
| Limonin | 12.5 |
| Limonin Glucoside | 75 |
| Glucoside Mixture | 0.08 |

These results suggest that the citrus limonoids tested are potential anti-cancer agents.

(b) Palm oil tocotrienols inhibit proliferation of MDA-MB-435 estrogen receptor-negative (ER−) as well as MCF-7 estrogen receptor-positive (ER+) human breast cancer cells at IC50s of 30–180 mg/ml in ER− cells and 2–125 mg/ml in ER+ cells. These cells are also inhibited by flavonoids, including genistein, hesperetin, naringenin and quercitin at IC50s of 18–140 ug/ml in ER− cells and 2–18 ug/ml in ER+ cells. The effect of two citrus flavonoids, tangeretin and nobiletin (from tangerines), alone and in 1:1 combinations with tocotrienols, with or without tamoxifen, was studied in both MDA-MB-435 and MCF-7 cells.

Materials—TRF and the individual tocotrienols were obtained from the Palm Oil Research Institute of Malaysia (PORIM), Kuala Lumpur. Hesperetin, nobiletin and tangeretin were obtained from State of Florida, Department of Citrus Lake Alfred, Fla. Apigenin, genistein, hesperetin, naringenin, quercetin and tamoxifen were purchased from the Sigma Chemical Co., St. Louis, Mo. Tissue culture medium, fetal calf serum and fingizone were purchased from Gibco, Burlington, ON. Fetal calf serum treated with dextran-coated charcoal (FCS/DCC) was obtained from Cocalico Biologicals Inc., Reamstown, Pa. [$^3$H] Thymidine was purchased from ICN, Irvine, Calif. MTT and all other chemicals were purchased from Sigma.

Cell Culture—MDA-MB-435 (estrogen receptor-negative) human breast cancer cells were maintained at 37° C. in minimum essential medium (alpha modification) containing 3.7 g of sodium bicarbonate per liter supplemented with 10% v/v fetal calf serum and 1% (v/v) fungizone (antibiotic/antimycotic), in humidified atmosphere of 5% carbon dioxide. Stock$_5$ cultures were seeded at a density of 2×10 cells and allowed to multiply for 48–72 hours. MCF-7 cells (estrogen receptor-positive human breast cancer cells) were maintained in the same medium as above, supplemented with 1 mM sodium pyruvate and 10 $\mu$g/mL insulin. The cells were grown at 37° C. in a humidified atmosphere containing 5% $CO^2$. Stock cultures were seeded at a density of 2×10 cells/mL and passaged weekly, using 0.25% trypsin.

Incorporation of [$^3$H] Thymidine Into DNA-MDA-MB-435 cells were plated at a density of 2×10$^4$ cells/well in 96-well, flat-bottomed plates in a total volume of 200 $\mu$L of medium and incubated at 37° C. for 48 hours, with or without the test compounds. [$^3$H] thymidine (0.5 $\mu$Ci/well) was then added to determine the number of dividing cells at each concentration and after 4 hours the cells were harvested onto a glass fibre filter paper using semi-automatic, 12-well cell harvester (Skatron Inc., Sterling, Va.). Radioactivity on the filter paper was counted, using BCS scintillant in a liquid scintillation counter. For the MCF-7 cells, the growth medium was exchanged for pheno red-free medium containing 10% fetal calf serum that had been treated with dextran-coated charcoal (FCS/DCC) five days prior to use. The cells were then trypsinized and 2×10$^4$ cells/well were plated as described above. After 2 days the medium was removed and the cells were incubated for 5 days in an experimental medium containing 2.5% FCS/DCC with or without the test compounds. [$^3$H] Thymidine (0.5 $\mu$Ci/well) was then added and the cells were harvested as described above. The concentration at which 50% inhibition occurred was determined by comparing the number of disintegrations per minute for the treated cells with that obtained for the control cells.

Growth Experiment—MDA-MB-435 and MCF-7 cells were plated at 1×10$^4$ cells/dish in 60 mm dishes with or without test compounds at their IC50 concentration in a total volume of 7 mL. The cells were removed by trypsinization at the specified times and counted, using a hemocytometer.

Results—Tangeretin and nobiletin inhibited these cells more effectively than other flavonoids tested to date, with an IC50 of 0.4 & 0.8 $\mu$g/mL respectively in the ER+ cells. When the flavonoids were tested in 1:1 combinations with tocotrienols, tangeretin and gamma-tocotrienol gave the lowest IC50s (0.05 $\mu$g/mL in ER– cells and 0.02 $\mu$g/mL in ER+ cells). The addition of tamoxifen also decreased the IC50 of 0.01 $\mu$g/mL in ER– cells but did not alter the IC50 in ER+ cells. Tamoxifen also decreased the IC50 for nobiletin and delta-tocotrienol from 0.8 to 0.001 $\mu$g/mL in ER+ cells. These results suggest that tocotrienols and citrus flavonoids are anti-cancer agents in the treatment of breast cancer.

7. EXAMPLE

Hypocholesterolemic Effects of Naringenin and Hesperetin in Rabbits and HEPG2 Cells (a) The effect of naringenin and hesperetin on casein-induced hypercholesterolemia was studied in rabbits. In each of the two experiments, rabbits were assigned to three experimental groups (FIG. 1). Each group was given semipurified, cholesterol-free casein diet and either water, orange juice or grapefruit juice to drink. Dextrose in the diets of the hesperitin (orange juice) and naringenin (grapefruit juice) groups was reduced to account for the sugar consumed via citrus juices. All other dietary components were left unchanged. Table 2.

TABLE 2

Average Pecentage Composition of Cholesterol-free Semipurified Casein Diets Fed to Rabbits.

| Ingredient | Diet | | |
|---|---|---|---|
| | Control | Orange Juice | Grapefruit Juice |
| Casein | 27.0 | 35.4 | 30.3 |
| Dextrose | 55.7 | 46.4 | 50.2 |
| Alphacel | 4.8 | 5.0 | 5.4 |
| Salt mixture (Phillips & Hart) | 4.0 | 4.2 | 4.5 |
| Molasses | 4.2 | 4.5 | 4.7 |
| Palm oil | 1.3 | 1.4 | 1.5 |
| Soy oil | 2.2 | 2.3 | 2.5 |
| Oil soluble vitamins | 0.5 | 0.6 | 0.6 |
| Water soluble vitamins | 1.5 | 1.6 | 1.7 |

Serum Analysis: At the end of the study, VLDL, LDL and HDL fractions were separated by discontinuous density gradient ultracentrifugation. Total cholesterol in serum and in each lipoprotein fraction were measured using the Boehringer Manheim CHOL kit (Manheim, Germany).

Liver Tissue Analysis: Total lipids were extracted from liver samples according to Folch et al., 1957, J. Biol. Chem. 226:497–509. Total and free cholesterol in lipid extracts were determined using the Boehringer Manheim kits.

Fecal Analysis: Feces collected for three days during the last week of the study were freeze-dried. Fecal neutral steroids were extracted with petroleum ether, following saponification. Fecal cholesterol in the extracts was quantified using the CHOL kit. Fecal bile acids were extracted with t-butanol and enzymatically quantified with 3a-hydroxysteriod dehydrogenase (van der Meer et al., 1985, In Cholesterol Metabolism in Human Disease Studies in the Netherlands, eds. A. C. Beynen, et al., 113–119).

(b) the effect of naringenin and hesperetin on metabolism of cholesterol in rabbits was studied using HepG2 cells in vitro.

Cell Culture: Confluent HepG2 cells were preincubated in minimum essential medium (MEM) containing 1.0% bovine serum albumin (BSA) for 24 hours. This was followed by a second 24 hour incubation with or without various non-toxic concentrations of naringenin or hesperitin (7.5–60 $\mu$g/ml). At the end of the second 24 hour incubation, the apoB content of the media was determined by enzyme-linked immunosorbent assay (ELISA) (Young et al., 1986, Clin. Chem. 32:1484–1490).

$^{14}$C-acetate Incorporation

To determine whether exposure to flavonoids can also alter intracellular lipid metabolism, confluent HepG2 cells were incubated for 24 hours with the highest apoB-reducing, non-toxic concentration of these flavonoids, in the presence of $^{14}$C-acetate (0.5 $\mu$Ci/ml medium). Radiolabelled lipids were then extracted from cells using heptane/isopropyl alcohol (3:2, v/v), and separated by thin layer chromatography. A hexane/ethyl ether/acetic acid solvent (75:25:1, v/v) was used to separate cholesterol, cholesterol esters and triglycerides. Lipid fractions were scraped into scintillation vials and the radioactivity was measured using Beckman Scintillation Counter.

Protein Determination: The soluble cellular protein was extracted and measured using Pierce Coomassie Plus Protein Assay.

Results: (a) In rabbits, replacement of drinking water with either grapefruit juice (naringenin) or orange juice (hesperetin) counteracted the rise in LDL cholesterol induced by dietary casein (FIG. 2).

The antihypercholesterolemic action of hesperetin (orange juice), but not naringenin (grapefruit juice), is associated with reduction of liver cholesterol. (Table 3)

TABLE 3

Total Cholesterol, Cholesterol Esters and Free Choesterol for Each Experiment

| Group (N) | Total Cholesterol (mg/g liver) | Cholesterol Esters (mg/g liver) | Free Cholesterol (mg/g liver) |
| --- | --- | --- | --- |
| Control 12 | $3.8 \pm 0.2^a$ | $1.2 \pm 0.2^c$ | $2.7 \pm 0.1$ |
| Orange 12 | $3.1 \pm 0.1^a$ | $0.7 \pm 0.1^d$ | $2.4 \pm 0.1$ |
| Grapefruit 11 | $3.4 \pm 0.2^a$ | $0.7 \pm 0.1^d$ | $2.7 \pm 0.1$ |

Values are means ± SEM. a,b,c,d = significant difference at p < 0.05 (One-way ANOVA, Bonferroni t-test)

The effect of dietary hesperetin or naringenin on cholesterol levels is unlikely to be related to increased fecal excretion of cholesterol and bile acids since there was no difference in these measurements between the three groups. Table 4.

TABLE 4

Fecal cholesterol and bile acid excretion for each experimental group.

| Group (N) | Cholesterol (mg/day) | Bile Acid (mg/day) |
| --- | --- | --- |
| Control 12 | $3.0 \pm 0.5^a$ | $10.5 \pm 1.5$ |
| Orange 12 | $1.7 \pm 0.3^b$ | $10.3 \pm 1.9$ |
| Grapefruit 1 | $1.5 \pm 0.3^b$ | $8.8 \pm 1.1$ |

Values are means ± SEM
a,b = significant difference p < 0.05 (One-way ANOVA)

(b) Naringerin and hesperitin present at high levels in citrus fruits have the ability to reduce overall production of apo-B in HepG2 cells. This effect is specific and not independent on reduction of cholesterol synthesis. FIGS. 3a, 3b and 4. These results in vitro indicate that naringenin and hesperetin influence metabolism of lipoproteins directly in liver.

The present invention is not to be limited in scope by the embodiments disclosed in the examples which are intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Various publications are cited herein, the disclosures of which are incorporated by reference in their entireties.

What is claimed is:

1. A pharmaceutical composition for treating breast cancer in a human subject, said composition comprising anti-neoplastic effective amounts of:

a citrus limonoid selected from the group consisting of limonin and nomilin, and a tocotrienol.

2. The pharmaceutical composition according to claim 1 further comprising a citrus flavonoid.

3. The pharmaceutical composition according to claim 1 wherein the citrus flavonoid is selected from the group consisting of nobeletin and tangeretin.

4. The pharmaceutical composition according to claims 1 or 2, wherein the tocotrienol is selected from the group consisting of alpha-tocotrienol, gamma-tocotrienol, and delta-tocotrienol.

5. A method of treating breast cancer comprising administering to a human subject in need thereof a pharmaceutical composition comprising anti-neoplastic effective amounts of:

a citrus limonoid selected from the group consisting of limonin and nomilin, and a tocotrienol.

6. The method according to claim 5, wherein the administered amount of the citrus limonoid in the range of 1 to 500 mg/day and the administered amount of the tocotrienol is in the range of 1 to 1200 mg/day.

7. The method according to claims 5, further comprising administering an anti-neoplastic effective amount of a citrus flavonoid.

8. The method according to claims 7, wherein the citrus flavonoid is selected from the group consisting of nobeletin and tangeretin.

9. The method according to claim 7, wherein the administered amount of the citrus flavonoid is in the range of 200 to 5000 mg/day.

10. The method according to claims 5 or 6, wherein the tocotrienol is selected from the group consisting of alpha-tocotrienol, gamma-tocotrienol, and delta-tocotrienol.

* * * * *